United States Patent [19]

Rolnick

[11] Patent Number: 4,681,094

[45] Date of Patent: Jul. 21, 1987

[54] BALLOON LARYNGOSCOPE

[75] Inventor: Michael A. Rolnick, Chevy Chase, Md.

[73] Assignee: American Medical and Emergency Research Corporation, Chevy Chase, Md.

[21] Appl. No.: 802,356

[22] Filed: Nov. 27, 1985

[51] Int. Cl.⁴ .............................................. A61B 1/26
[52] U.S. Cl. ...................................................... 128/10
[58] Field of Search ........................................ 128/4–8, 128/10, 11, 200.26

[56] References Cited

U.S. PATENT DOCUMENTS

| | | | |
|---|---|---|---|
| 1,498,810 | 6/1924 | Poe | 128/200.26 |
| 1,567,500 | 12/1925 | Hein | 128/207.15 |
| 1,664,660 | 4/1928 | Cameron | 128/4 |
| 1,705,513 | 3/1929 | Wappler | 128/4 |
| 2,127,215 | 8/1938 | Gwathmey | 128/208 |
| 2,354,471 | 7/1944 | Macintosh | 128/10 |
| 2,687,719 | 8/1954 | Hoyt | 128/38 |
| 2,705,959 | 4/1955 | Elmore | 128/351 |
| 2,756,742 | 7/1956 | Barton | 128/15 |
| 3,154,069 | 10/1964 | Ring | 128/15 |
| 3,259,132 | 7/1966 | Katter | 128/344 |
| 3,306,298 | 2/1967 | Raimo | 128/351 |
| 3,543,751 | 12/1970 | Sheffer | 128/208 |
| 3,698,391 | 10/1972 | Mahony | 128/261 |
| 3,734,100 | 5/1973 | Walker et al. | 128/351 |
| 3,756,244 | 9/1973 | Kinnear et al. | 128/351 |
| 3,800,788 | 4/1974 | White | 128/83 |
| 3,882,852 | 5/1975 | Sinnreich | 128/4 |
| 3,930,507 | 1/1976 | Berman | 128/345 |
| 3,993,081 | 11/1976 | Cussell | 128/351 |
| 4,040,413 | 8/1977 | Ohshiro | 128/6 |
| 4,041,936 | 8/1977 | Carden | 128/6 |
| 4,091,816 | 5/1978 | Elam | 128/351 |
| 4,112,936 | 9/1978 | Blachly | 128/136 |
| 4,126,127 | 11/1978 | May | 128/11 |
| 4,198,970 | 4/1980 | Luomanen | 128/207.15 |
| 4,244,362 | 1/1981 | Anderson | 128/200.26 |
| 4,306,547 | 12/1981 | Lowell | 128/11 |
| 4,315,505 | 2/1982 | Crandall et al. | 128/200.26 |
| 4,329,983 | 5/1982 | Fletcher | 128/207.14 |
| 4,356,821 | 11/1982 | Rind | 128/207.14 |
| 4,384,570 | 5/1983 | Roberts | 128/4 |
| 4,517,962 | 5/1985 | Heckele | 128/6 |
| 4,573,460 | 3/1986 | Szachowicz et al. | 128/200.26 |

FOREIGN PATENT DOCUMENTS

| | | | |
|---|---|---|---|
| 154241 | 9/1938 | Austria | 128/5 |
| 3273 | of 1899 | United Kingdom | 128/200.26 |
| 445218 | 4/1936 | United Kingdom | 128/208 |

OTHER PUBLICATIONS

Special Anesthetic Techniques in Head and Neck Surgery, Allan C. D. Brown, M.B. et al., vol. 14, No. 3, Aug. 1981, pp. 587–614.

Special Equipment in the Operating Room for Otolaryngology–Head and Neck Surgery, Robert T. Sataloff, M.D. et al., vol. 14, No. 3, Aug. 1981, pp. 669–686.

Primary Examiner—Kyle L. Howell
Assistant Examiner—Max F. Hindenburg
Attorney, Agent, or Firm—Dennison, Meserole, Pollack & Scheiner

[57] ABSTRACT

A laryngoscope comprising a disposable blade unit including two full length blades releasably interconnected along the length thereof to define a tubular passage. A reusable handle unit removably receives one end of the blade unit and retains the blades thereof. The blade unit includes an inflatable balloon expandable against the roof of the mouth to center an inserted laryngoscope and effect movement thereof against the tongue and epiglottis. A pair of suction channels are defined through the blade unit and communicated with the interior of the tubular passage at the leading end thereof. The handle unit includes means for communicating the balloon and suction passages with sources of positive and negative air pressure respectively. The handle unit also mounts illuminating means and a selectively usable adapter for accommodating a hand manipulable air bag for emergency respiration directly through the laryngoscope.

34 Claims, 11 Drawing Figures

BALLOON LARYNGOSCOPE

BACKGROUND OF THE INVENTION

The invention herein generally involves medical devices, and more particularly concerns devices for the reestablishment of an air passageway through the throat effected initially by the introduction of the device itself followed by intubation, the introduction of an endotracheal tube into the trachea. Such devices are commonly referred to as laryngoscopes and, in use, are intended to provide a direct line viewing or exposure of the larynx by a pushing back or retracting of the tongue, epiglottis and other soft structures within the mouth.

As frequently occurs with a critically ill, anesthetized or injured patient, the normal spontaneous respiratory function is affected and could result in a life threatening situation. Under such circumstances, provision must be made for introducing air into the lungs to prevent suffocation. This is normally effected by the placing of a tube through the mouth and into the larynx or trachea to define an open airway through which the attending person can pump air to inflate the lungs and assist in breathing. The actual introduction of the air can be effected by a manual bag pump, as is frequently used in emergency respiratory equipment, or through use of a mechanical pumping device. In using breathing apparatus, it is essential that the windpipe or trachea be kept clear of food or other substances which might affect the free air flow sought. This function, under normal breathing circumstances, is performed by a fleshy, flaplike cover over the trachea, called the epiglottis.

In situations where an airway must be established and maintained, the patient is most frequently in a semi-conscious or unconscious state, usually lying on his back. Unfortunately, in this position, the lax tongue of the patient tends to fall back into the throat blocking the epiglottis and closing off the windpipe. Therefore, in order to insert the airway or endotracheal tube, the physician frequently relies upon a device called a laryngoscope. The laryngoscope will normally be positioned within the mouth in a manner so as to move the tongue to a non-blocking position, lift the epiglottis away from the windpipe, and provide for a visual view of the opening of the trachea, normally in the vicinity of the vocal chords, to allow for a manual insertion of the endotracheal tube. As will be readily appreciated, it is important that this procedure be performed as rapidly as possible and air flow reestablished and maintained to prevent permanent injury or asphyxiation.

Under current practice, when breathing difficulty occurs, either through injury, illness or when under anesthesia, the patient is, if possible, placed on his back. A breathing device, normally a mask with a connected air bag, is fitted over the patient's mouth and the air bag pumped to force air into the mouth and lungs. However, in most emergencies, adequate breathing cannot be maintained by the bag mask unit and the insertion of an endotracheal tube is usually required. In such cases, the physician or attending person will use the air bag to provide enough air to the lungs to sustain life, and then attempt to insert a laryngoscope to clear a passageway for the subsequent introduction of an endotracheal tube.

While the known art relating to laryngoscopes is quite extensive, the most commonly used laryngoscope is an L-shaped device with a handle section, normally incorporating batteries and being similar in appearance to a flashlight handle. The second section of the device consists of a curved or straight metal blade approximately 10" long and capable of being inserted into the mouth, down the throat and past the epiglottis. Frequently, a light bulb will be provided at the end of the blade. In use, the blade is inserted over the back of the tongue, down the throat and under the epiglottis. The handle is then lifted, lifting the blade, tongue and epiglottis, and thereby unblocking the windpipe opening. Upon obtaining a clear view of the windpipe opening, the tracheal tube is inserted along the laryngoscope blade and the desired flow of air induced through the tube by appropriate mechanical means until such time as the patient is capable of normal breathing.

The use of a conventional laryngoscope involves, at best, a troublesome procedure whereby great care must be taken to avoid internal damage to the mouth and throat membranes while at the same time effectively engaging, moving and maintaining the relatively large tongue mass and epiglottis until such time as the endotracheal tube is intubated. The procedure is frequently complicated by the presence of mucus, blood, vomitus, and the like which must be removed or at least prevented from entrance into the windpipe.

The conventional laryngoscope is also a relatively expensive metal device which is adapted for reuse, and thus gives rise to problems of sterilization. Such problems are increased in those instances wherein a light emitting bulb is provided at the leading end of the blade. The presence of such a bulb at the inserted tip of the laryngoscope may also give rise to the possibility of localized burns to the sensitive membranes.

In view of the generally firm manual manipulation required in the use of a conventional laryngoscope, great care must also be taken to avoid damage to the teeth of the patient.

SUMMARY OF THE INVENTION

The laryngoscope of the present invention presents multiple structural and functional advantages in providing for an effective emergency restoration of breathing. Such advantages, which are the principal objects of the invention, include the provision of a laryngoscope wherein the component portion thereof received within the throat of the patient is specifically constructed for single use as a disposable item formed of relatively low cost plastic which, while of a sufficient rigidity to open and maintain an air passage, and provide continuous visualization, incorporates a degree of resiliency or flexibility which makes the device substantially less likely to damage mouth tissue, teeth and the like.

It is also a significant intention of the invention to provide for the necessary tongue and epiglottis depression in a controlled manner with the laryngoscope, in effect, self-centering within the mouth with minimal force, membrane trauma, and the like.

In regard thereto, the proper insertion and positioning of the laryngoscope of the invention can be effected with minimal training, thus allowing for substantially universal use.

Upon insertion, the laryngoscope is uniquely adapted for instantaneous use as an air way, prior to actual intubation, should such be required as emergency treatment. Basically, this is achieved by the provision of means for the direct attachment of an air introducing and lung inflating air bag or hand pump to the laryngoscope for a rapid introduction of air through the tubular passage which normally receives the endotracheal tube.

After an initial life-sustaining introduction of air, the attendant can proceed with the actual intubation.

With regard to the emergency introduction of air, as well as the subsequent intubation, the positioning of the laryngoscope itself provides for a positive seal thereabout, primarily through the inflation balloon and the self-centering nature of the laryngoscope, to insure maximum effective air flow.

The provision of a reusable handle unit in conjunction with a disposable blade unit is significant in that the major control components and air flow sources can be incorporated in, attached to and controlled from the handle unit which, being exterior of the mouth, is subjected to minimal contamination and can be readily sterilized for reuse. At the same time, the blade unit, subjected to maximum contamination, is so constructed as to comprise a relatively inexpensive item which, other than for the air pressure responsive balloon, has no controls, active components, or the like, notwithstanding the unique construction thereof which provides inherent self-centering functions. Such self-centering functions minimize physical external manipulation of the laryngoscope other than for the actual insertion of the laryngoscope and preliminary alignment thereof.

In order to achieve the particular advantages of the invention, the laryngoscope basically comprises a disposable blade unit and a reusable handle unit. The blade unit includes two blades, one directed toward the tongue and including a transversely arcuate external configuration for centrally accommodating and conforming to the tongue. The second blade includes an inflatable balloon, along a substantial portion of the length thereof inward from the leading or distal end. The balloon is particularly adapted to, upon inflation, expand against the roof of the mouth, centering on the arch thereof and exerting a controlled pressure over a substantial area of the mouth roof to effect a movement of the laryngoscope against the tongue and epiglottis in a manner so as to effect a passage clearing movement thereof.

The blades of the disposable blade unit define a full length tubular passage therethrough for visualization and reception of the endotracheal tube during intubation. This passageway is also capable of acting as a temporary airway. The blade unit further includes a pair of suction channels paralleling the tubular passage immediately outward thereof.

The laryngoscope additionally comprises a reusable handle unit which receives and maintains the joined blades. The handle unit includes means for direct engagement with sources of positive pressure for balloon inflation, negative pressure for suction operation and others depending upon additional features desired. For example, it is particularly intended that the laryngoscope be provided with illumination. As such, the handle unit will directly incorporate a pair of illuminating bulbs, each appropriately supplied with electric current, preferably battery supplied. Likewise, it is intended that the laryngoscope be capable of providing for the emergency introduction of air prior to actual intubation. As such, the handle unit will incorporate an adapter which can be selectively and rapidly positioned over the proximal end of the intubation tubular passageway for the mounting thereon of an air bag or hand pump of the type normally associated with resuscitation mask assemblies. The adapter will preferably be confined to allow for continued visualization through the tubular passageway as emergency air is introduced therethrough. The laryngoscope of the invention, in conjunction with the inflated balloon will, in itself, prevent leakage and allow immediate air introduction and lung inflation without requiring a separate application of a mask.

The blade unit is specifically configured to key within the handle unit to preclude improper orientation or mounting. This is particularly significant in that the fluid or air pressure lines are joined, between the handle unit and blade unit, through the simple although unique expedient of merely seating the blade unit within the handle unit. As an additional advantage, the air lines in the blade unit, and in particular the air line to the inflated balloon, can be instantaneously vented, and the balloon deflated, by merely a removal of the handle unit.

Additional objects, particularly with regard to the manner of use and advantages of the laryngoscope of the invention, will become more apparent from the more detail description of the invention following hereinafter.

DESCRIPTION OF PREFERRED EMBODIMENT

Referring now more specifically to the drawings, reference numeral 20 is used to generally designate the laryngoscope comprising the present invention. The laryngoscope 20 basically comprises a disposable insertion blade unit 22 and a reusable handle unit or holder 24.

The blade unit 22 includes two elongate overlying blades designated by their orientation within the mouth of a patient as a chin blade 26 adapted to overlie and engage the tongue 28, and a nose blade 30 directed toward and immediately underlying the roof of the mouth.

The chin blade 26 is of a transversely arcuate configuration, both exteriorly and interiorly, along the full length thereof, and defines an internal full length arcuate channel 32. The channel opens through both the distal end 34 of the blade, that end corresponding with the distal or leading end 36 of the laryngoscope 20, and a proximal or rear end 38 which engages within the holder 24 as shall be explained subsequently.

The proximal end 38 of the chin blade 26 includes an integral rectangular mounting flange 40 projecting laterally beyond the opposed sides of the blade 26 and including a straight outer edge 42 generally tangential with the midpoint of the arcuate outer surface of the blade 26.

Figure 7:
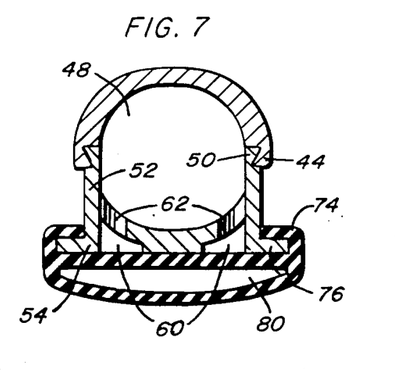
FIG. 7 is an enlarged cross-sectional detail taken substantially on a plane passing along line 7—7 in FIG. 4.
Figure 8:
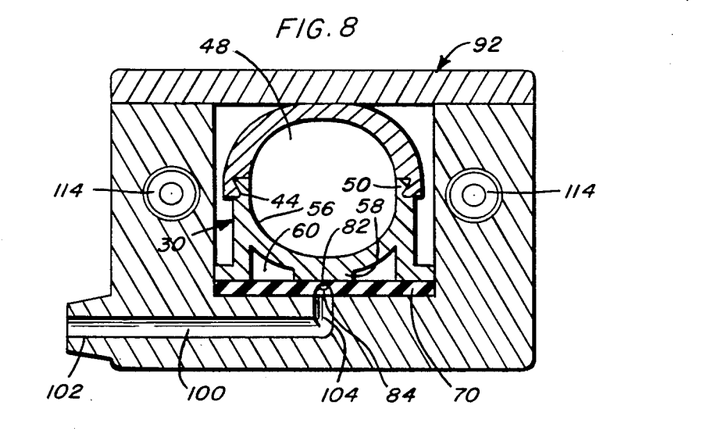
FIG. 8 is an enlarged cross-sectional detail taken substantially on a plane passing along line 8—8 in FIG. 4.

The chin blade 26 is to be releasably engaged with the nose blade 30 along the length thereof. As such, the opposed longitudinal edges 44 of the chin blade 26 include a snap-lock configuration comprising basically an inwardly directed undercut lip best illustrated in FIG. 10 and the cross-sectional details of FIGS. 7-9. It will be noted that this snap-lock configuration is continuous through the flanged end of the blade 26.

The nose blade 30, that blade directed toward the roof of the mouth, and hence the nose, also defines a full length arcuate internal channel 46 which compliments the channel 32 and forms therewith a tubular passageway 48. As best noted in FIGS. 6-9, the tubular passageway 48 is preferably slightly oblong in cross-section, as is the exterior of the chin blade 26, to facilitate insertion, provide for more convenient engagement with the tongue, and most specifically, to enhance visibility along the straight length therethrough prior to and during intubation. In order to achieve the desired releasable interengagement between the blades 26 and 30, the opposed longitudinal edges 50 of the nose blade 30 are provided with snap-lock configurations in the nature of undercut outwardly directed lips which cooperate with the lips along the edges 44 of chin blade 26 allowing a snap interlocking and disengagement or, alternatively, a sliding engagement and release. A sliding release will, as a practical matter, probably best facilitate withdrawal of the blade unit 22 after intubation.

Figure 5:
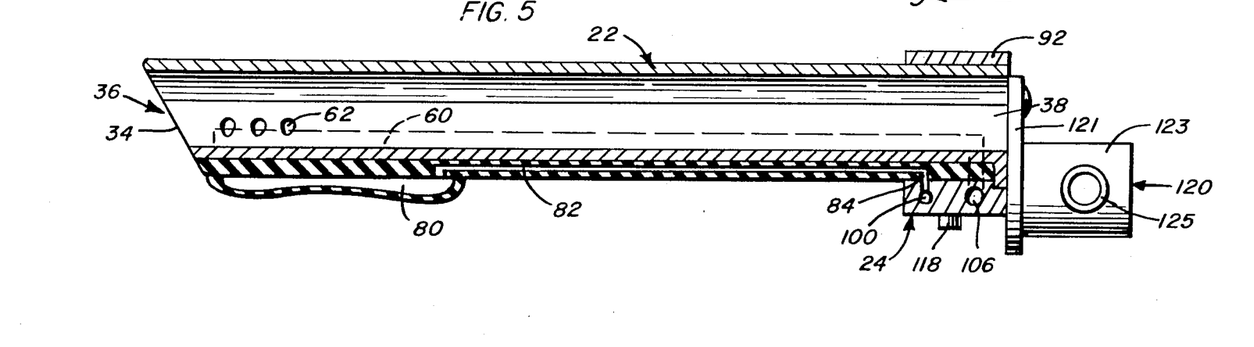
FIG. 5 is a longitudinal cross-sectional view through the laryngoscope.
Figure 6:
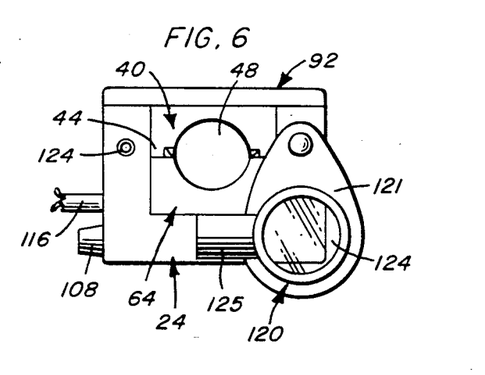
FIG. 6 is an end elevational view taken from the right end of FIG. 4.

The opposed sides or side walls 52 of the nose blade 30 are planar and terminate in edges 54 outward of the outermost central extent of the substantially arcuate wall 56 which defines the channel 46. The arcuate wall 56 is in turn provided with a central substantially full length outwardly directed rib 58. Each side wall 52, between the side wall and the central rib 58, defines an elongate suction channel 60 sealed at the opposed ends thereof immediately adjacent the distal and proximal ends of the nose blade 30. Noting FIGS. 5, 7 and 10, appropriate fluid and material passing holes 62 communicate the forward ends of the suction channel 60 with the interior of the nose blade channel 46, and hence the formed tubular passageway 48 adjacent the open distal end of this passageway.

The proximal end of the nose blade 30 is provided with an integral mounting flange 64 similar to the flange 40. The flange 64 is of generally rectangular configuration projecting outwardly of the open end of the arcuate channel 46 and includes edges 66, to the opposed sides of the channel 46, which provide for line contact with similar edges on the flange 40, and an opposed full length edge 68 projecting beyond the outer edges 54 of the side walls 52 and the rib 58 therebetween, defining in effect a positioning lip. The two mounting flanges 40 and 64, upon a joining of the blades 26 and 30, form a rectangular planar mounting and positioning plate.

Overlying the nose blade 30, along the full length of the side thereof opposed from the channel 46, is a rubber-like elastomeric panel or pad 70 sealed to the edges 54 of the side walls 52 and to the central rib 58, preferably by pressure contact therewith, to enclose the suction channels 60 in a substantially airtight manner. The pad 70, adjacent the proximal end of the nose blade 30, and slightly forward of the end mounting flange 64, includes a pair of holes 72 therethrough opening through the pad and into the two suction channels 60.

The mounting of the pad or panel 70 is normally effected by a pair of opposed reentrant or reversely turned longitudinal edge flanges 74 which extend rearwardly from the distal end of the pad 70 and engage about integral laterally outwardly extending flanges 76 along the edges 54 of the side walls 52. The reentered flanges 74 of the pad 70 terminate short of the proximal ends of the wall flanges 76. The wall flanges 76, noting FIG. 11 in particular, terminate at different distances from the mounting flange 64, defining in effect different width positioning notches 78 which insure proper mounting of the blades 26 and 30 as shall be explained subsequently.

The elastomeric pad or panel 70, inwardly from the distal end thereof, between the reentrant flanges 74 and for approximately one-quarter to one-half the length thereof, mounts an inflatable elastomeric balloon 80 adapted, upon insertion of the laryngoscope, to engage against and, on inflation, exert pressure against the roof of the mouth to effect the tongue repositioning required. Air flow to and from the interior of the balloon 80 will be preferably provided through an air line or passage 82 extending longitudinally through the pad 70 from the balloon toward the proximal end thereof, terminating in a laterally directed opening 84 through the pad 70.

Figure 1:
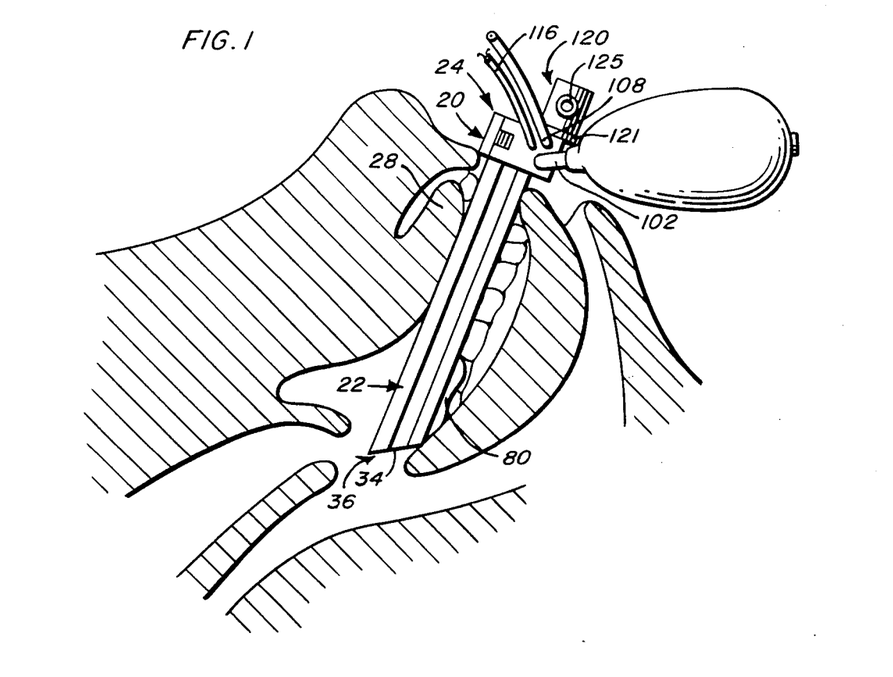
FIGS. 1 and 2 schematically illustrate the in use position of the laryngoscope of the invention with the patient supine and the head extended.
Figure 2:
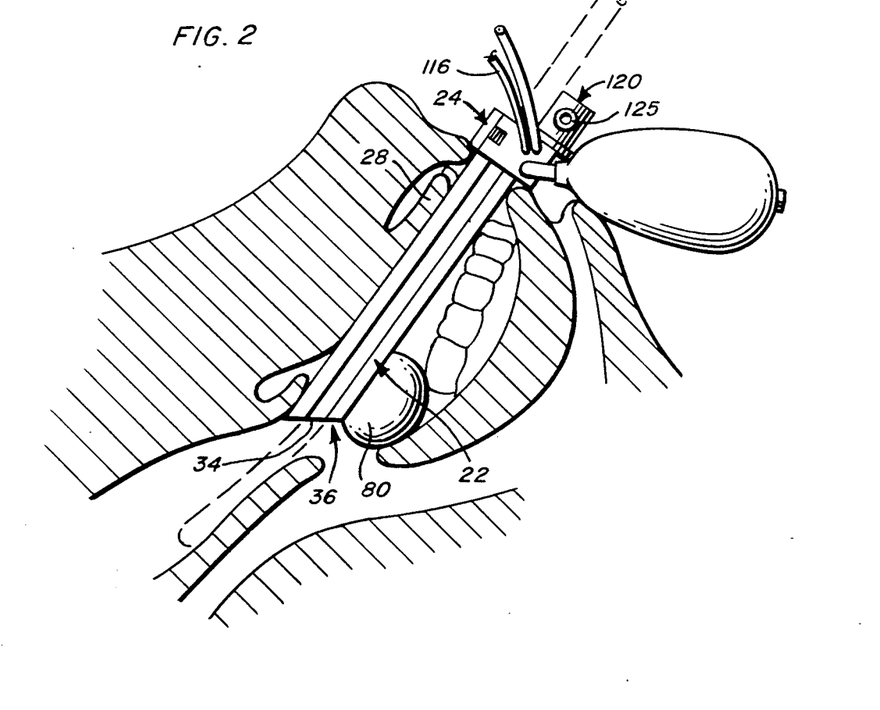
Figure 3:
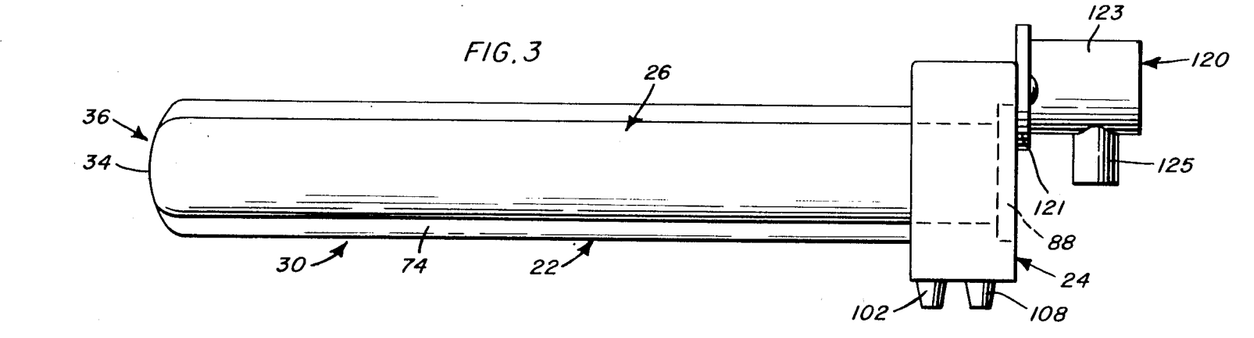
FIG. 3 is a plan view of the laryngoscope with the tongue engaging blade uppermost.
Figure 4:
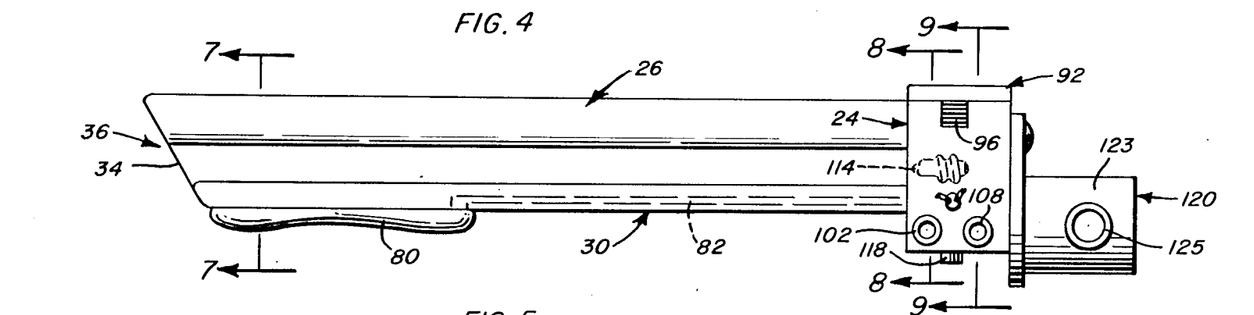
FIG. 4 is a side elevational view of the laryngoscope.

As best seen in FIGS. 1 and 2, the distal end of the blade unit 22 of the laryngoscope is cut or beveled with the rearwardly offset portion thereof directed toward the roof of the mouth to generally follow the line of the rear of the throat and reduce any tendency for traumatizing contact therewith while at the same time providing for maximum reach to engage the tongue and epiglottis.

Turning now to the handle unit or holder 24, this unit is in the nature of a rectangular block with a U-shaped seat 86 defined thereacross for reception of the proximal ends of the blades of the blade unit 22. The near end of the seat 86 includes a recess 88 thereabout which receives the bottom and side edges of the combined face mounting flanges 40 and 64 of the blades 26 and 30. Immediately inward of the edge recess 88, the seat 86 includes a pair of opposed blocks 90 adapted for reception within the opposed edge notches 78 of the nose blade 30. These blocks 90 are of different widths, corresponding to the different widths of the notches 78 whereby a proper alignment of the blade unit 22 within the holder 24 is assured. In other words, the blocks 90 and notches 78 key together in only one position with the mounting flanges 40 and 64 simultaneously received within the edge recess 88.

The proximal end of the blade unit 30 is secured within the holder 24 by a latch 92, normally pivoted, as at 94, to one leg of the block and snap engaged, as at 96, to the opposite leg. The height of the holder legs, relative to the blade unit 22, are such as to produce a positive clamping of the holder unit within the block upon a closing of the latch 92. This is particularly desirable in providing for a pressed sealing of holder received portion of the pad 70 of the nose blade 30 against the base 98 of the recess 86. This sealed relationship is desirable in that pressurization, both negative and positive, within the suction channels 60 and the balloon 80 is effected through the block of the holder 24.

Noting FIGS. 5 and 8-10, a first air passage 100 extends through the block of the holder 24 from an external mounting nipple 102 to a laterally turned inner end portion 104 opening through the base 98 of the seat 86 in alignment with the air passage or air line opening 84 for communication with the air line 82 therethrough and consequently with the interior of the inflatable balloon 80. The external nipple 102 will in turn mount a source of pressurized air, normally a hand manipulable air bag for a manually controlled inflation of the balloon 80. It might be noted at this time that when it becomes desirable to withdraw the laryngoscope 20, the balloon 80 will automatically vent and deflate upon release and removal of the holder 24, thereby opening the air line opening 84 to atmosphere.

The holder includes a second internal passage 106 therein, also preferably extending from a side mounted nipple 108 and including two laterally directed extensions 110 which open through the base 98 of the seat 86 in alignment with the holes 72 in the pad 70 which in turn directly communicate with the suction channels or chambers 60. This passage 106 constitutues a suction line communicated, through the external mounting nipple 108, with a suitable source of reduced pressure for the drawing of fluids and foreign substances, as encountered by the leading end of the laryngoscope, inwardly through the openings 62 thereat and subsequently through the suction channels 60 for appropriate discharge.

Figure 9:
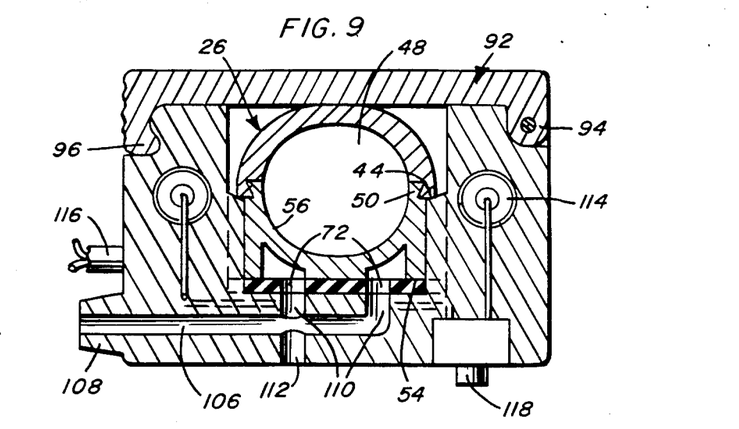
FIG. 9 is an enlarged cross-sectional detail taken substantially on a plane passing along 9—9 in FIG. 4.

As noted particularly in FIG. 9, a third lateral extension 112 of the suction passage 106 within the holder 24 communicates with the exterior of the holder block, providing a vent for the suction passage whereby manual control of the suction generated within the suction channels 60 can be easily manually controlled by a selective positioning of a finger over the venting extension 112. In other words, a complete closing of the vent 112 will direct the full force of the generated suction to the suction channels. Conversely, a completely open vent 112 will result in little or no suction action within the suction channels. In this manner, a positive, quick and exact control over the generation of negative pressure within the leading portion of the laryngoscope is achieved without necessitating a removal of the user's hand from the laryngoscope and without the necessity of manipulating of remote controls.

As will be appreciated, the source of negative pressure can comprise any appropriate medical pump means well known in the art. The nipples 102 and 108 can be differently configured, as deemed appropriate to facilitate proper component mounting.

Figures 10, 11:
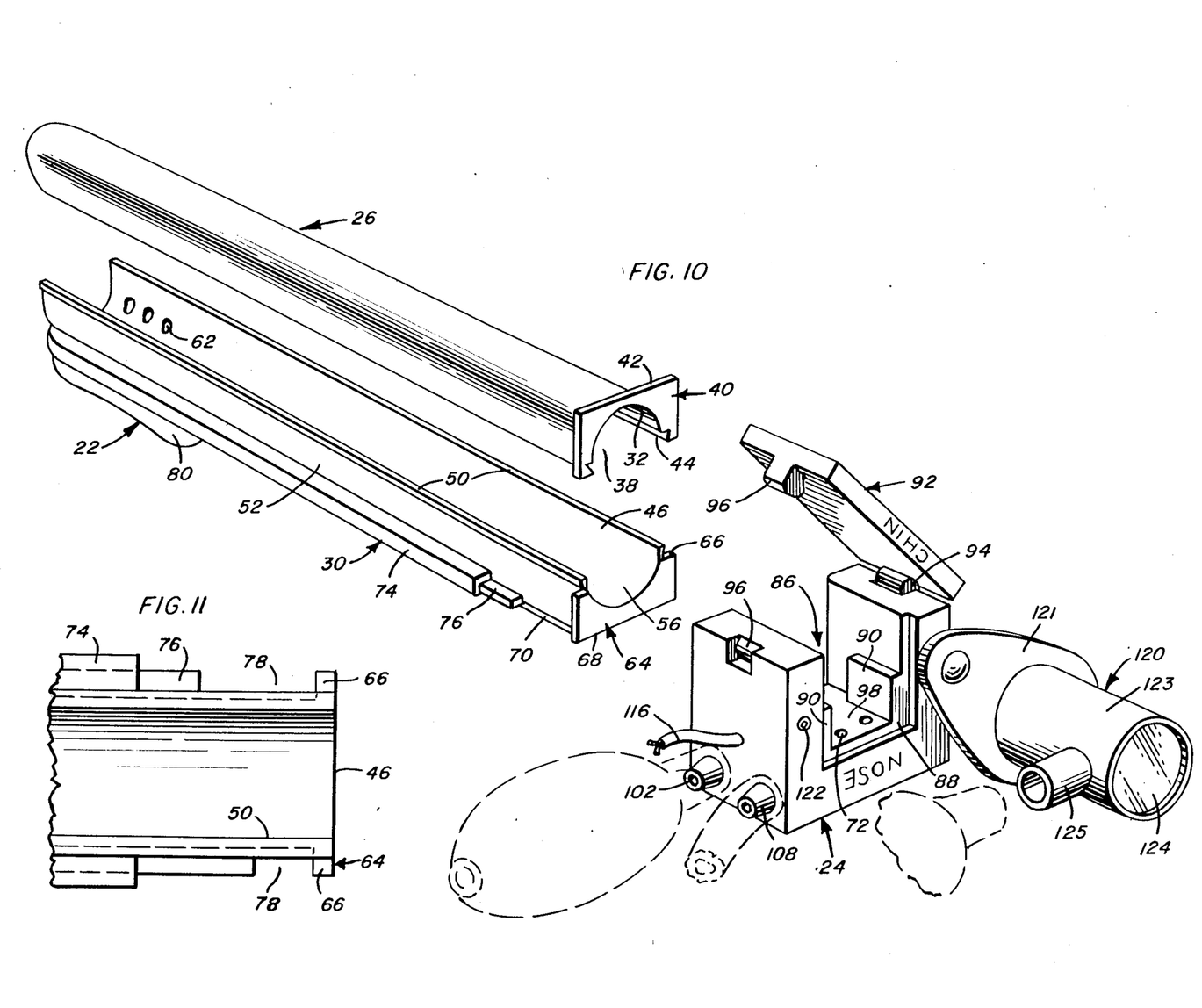
FIG. 10 is an exploded perspective view of the components of the laryngoscope.
FIG. 11 is a partial top plan view of the mounting end portion of the nose blade, or that blade directed toward the roof of the mouth.

The holder 24 also incorporates a light source, normally in the nature of a pair of bulbs 114 mounted in the block body and directed forwardly along the opposed sides of the blade unit 22. FIGS. 9 and 10 illustrate electric current providing wiring 116 and a finger controlled button or switch 118 for selective illuminating of the bulbs. The actual power source can either be line electric power or an appropriate battery pack. It will be appreciated that by mounting the illumination system within the holder 24, the illumination system is part of the reusable component and independent of the disposable blade unit 22.

It is also preferred that the handle unit or holder 24 include an air bag adapter 120 mounted on a swinging panel or lever 121 pivoted to the near face of the holder to selectively swing over the face of the holder and into alignment with the open proximal end of the tubular passage 48 defined by the two blades 26 and 30. As desired, an appropriate detent arrangement 122 can be provided to hold the adapter lever 121 in position. Basically, the adapter 120 includes a straight tube 123 mounted on the panel 121 for alignment with the tubular passageway 48. The outer end or end wall 124 of the tube 123 is hermetically sealed and transparent to provide for straight visualization through tube 123 and passageway 48. The operational mounting of an air bag or similar pressurizable source of breathable fluid is provided for by a laterally directed mounting nipple 125 on the adapter tube 123. The nipple 125 allows for the introduction of emergency air without interfering with the visualization of the internal site through the end wall window 124. The adapter 120, when positioned in alignment with the tubular passage through the laryngoscope, allows for emergency resuscitation using a conventional means, such as an air bag, without necessitating the mounting of a mask over the face of the patient. Such an air bag is suggested in phantom lines in FIG. 10. Thus, in an emergency situation, the patient's lungs can be quickly filled with air prior to intubation as a life saving step. While the seal between the adapter 120 and the end of the tubular passage through the blade unit will not be perfect, it will be sufficient to insure an adequate flow of air through the laryngoscope.

Similarly, if preliminary inflation of the balloon 80 has been achieved, this will tend to control air leakage about the mouth.

In use, a disposable blade unit 22, with the blades 26 and 30 normally pre-assembled, is mounted within the reusable handle unit 24 and locked therein by the swinging lock bar 92. The laryngoscope 20 is then ready for insertion within the throat of the patient. In regard thereto, please note the desirability, as indicated in FIG. 10, of actually labelling the handling unit or holder 24 with the terms CHIN and NOSE. In this manner, there should be no possibility of improper introduction of the laryngoscope with the balloon 80 directed other than toward the roof of the mouth. Actual insertion can be facilitated by a coating of the outer surfaces of the blade unit with a suitable lubricant.

With the patient preferably supine and the head, if possible under the particular circumstances involved, extended, generally as noted in FIGS. 1 and 2, the blade unit is slid into the mouth until the lips touch the holder. Observing the NOSE-CHIN indications on the holder, the balloon will be oriented to the roof of the mouth. The balloon is then inflated, preferably by the use of a hand squeezed air bag or hand bulb which as a matter of expediency, will normally be permanently attached at the nipple associated with the air flow passage to the balloon. A squeezing of the hand bulb approximately three times will bring about the desired inflation.

The oval configuration of the chin blade 26 will facilitate its inward movement over the tongue, centering on the tongue as it moves into the throat and toward the back thereof. As the balloon is inflated, the blade unit 22 pushes the oval chin blade 26 against the tongue, moving the tongue, and subsequently lifting the epiglottis to open the patient's airway. An actual pivotal movement of the external holder 24 will be noted as the balloon inflates. In fact, if no movement of the holder is noted, the laryngoscope should be removed and the balloon checked.

The inner end of the laryngoscope should be positioned vertically directly over the vocal chords. This can be accomplished by selectively inflating or deflating the balloon through manipulation of a conventional inflation hand bulb, normally incorporating an appropriate valve for deflation purposes. Lateral positioning of the laryngoscope will be effected automatically by engagement of the inflated balloon with the arched roof of the mouth. The lights provided on the holder allow a viewing down the center of the tube to both properly position the laryngoscope relative to the vocal chords and determine whether suction is necessary for the removal of mucus, blood, vomitus and other foreign matter. As previously indicated, control of the suction can be easily effected by one hand on the holder selectively opening and closing the vent passage or bypass opening. The provision of two bulbs is significant in insuring proper illumination of the work site even should one bulb be blocked or otherwise disabled.

As the balloon inflates, there is a tendency for the laryngoscope to pivot with the inner end thereof moving against the tongue and epiglottis and with the outer end tending to press against the teeth. Any possibility of damage to the teeth is substantially reduced or eliminated by the presence of the elastomeric pad 70 which extends from the balloon to and into the holder recess, defining in effect a bite block. If deemed appropriate, the pad, in the area of engagement with the teeth, can in fact be slightly thickened.

Subsequent to insertion of the laryngoscope and insertion of the balloon, should emergency ventilation be required prior to intubation of the endotracheal tube, the adapter 120 is swung into position over the proximal open end of the laryngoscope and an air bag connected thereto and manually manipulated to force air into the lungs, much as is conventionally done with a mask and air bag assembly but without necessitating use of the mask and without affecting visualization. Inflation of the balloon itself seals the mouth, filling the mouth cavity and minimizing dead air space, thus improving ventilation effectiveness.

When the patient is ready to accept placement of the endotracheal tube, the air bag is removed and the adapter 120 swung out of the way, a visual inspection is again made to determine whether additional suction withdrawal of extraneous matter is necessary and to insure the continued proper positioning of the laryngoscope for introduction of the endotracheal tube into the trachea. Proper positioning, in light of the transversely arcuate nature of the chin blade 26 and the engagement of the inflated balloon with the arch of the mouth roof, should be effected automatically and easily maintained.

Assuming all is in order, the endotracheal tube is slid through the oval tubular passageway 48 directly into the windpipe or trachea opening.

After the endotracheal tube is properly positioned and secured, the laryngoscope can be removed. Basically, the locking bar is released and swung out of position allowing removal of the reusable holder. Removal of the holder immediately vents the air line to the balloon, causing a deflation thereof. The blades, at that point, can be removed and disposed of. As a matter of convenience, the blades can be either snapped apart and individually removed, or slid outward one relative to the other, in each case separating from the tube received therebetween. Upon removal, the holder or handling unit can be washed with soap and water to remove foreign material and subsequently appropriately disinfected for reuse.

While the holder or handle unit 24 has been presented as a block, it will be appreciated that this unit can assume other configurations while retaining the basic functions described including means for insuring proper orientation of the components relative to each other and of the laryngoscope within the mouth, and means for controlling the various pressurization and suction functions rapidly and effectively directly from the handle unit. In regard thereto, it is considered particularly significant that the positioning balloon will automatically deflate upon a release of the holder. Similarly, the physician can effectively control the amount of suction applied by merely positioning a finger selectively over the suction line vent hole. This can be done without diverting any attention away from the patient.

The use of an inflatable balloon as the positioning means for the laryngoscope is particularly advantageous in that the uniform distribution of pressure through balloon engagement with the roof of the mouth tends to eliminate any possibility of mouth damage or trauma. At the same time, the inflating balloon, in cooperation with the natural arch of the mouth roof, provides for a self-centering of the laryngoscope with the oblong curvature of the chin blade accommodating the natural curvature of the tongue as the tongue is shifted to open the airway. The use of the balloon provides, through a distribution of the load over a substantial area, maximum leverage with a minimum of force. The entire construction of the laryngoscope is particularly adapted for rapid and effective use by personnel with minimum training. Further, the specific construction of the laryngoscope allows for emergency ventilation using a conventional air bag, without the mask, at any time up to actual insertion of the endotracheal tube in that the blade unit of the laryngoscope actually defines an airway itself.

While it is preferred that the patient be supine with the head extended, the particular nature of the laryngoscope of the invention does provide for use in other positions as might be required in suspected cases of cervical injuries or in particularly cramped quarters.

The foregoing is considered illustrative of the principles of the invention. As variations and modifications may occur to those skilled in the art, it is to be appreciated that the invention is not limited to the exact construction and manner of use shown and described. Rather, the invention should only be limited by the scope of the claims following hereinafter.

I claim:

1. A laryngoscope comprising a blade unit, said blade unit including a distal leading end and a proximal handling end, an elongate tubular passageway defined through said blade unit for selective reception of an endotracheal tube therethrough, said tubular passageway opening through said distal and proximal ends, said blade unit having opposed first and second longitudinal outer surfaces respectively engageable with the tongue and mouth roof of a patient, said second surface including an inflatable positioning balloon along a portion thereof rearward from said distal end, and means for selectively inflating said balloon for outward expansion of said balloon into pressure engagement against a mouth roof thereby providing a fulcrum for movement of the first surface toward and against an opposed tongue and for simultaneous establishment of an airway and visual path to the trachea while precluding significant dental contact forces.

2. The laryngoscope of claim 1 wherein said blade unit comprises plural elongate blades, means for releasably connecting said plural blades to define said tubular passage, said means for connecting said blades allowing movement of said blades relative to each other for selective disengagement and removal from a received endotracheal tube.

3. The laryngoscope of claim 2 wherein said blades comprise first and second blades, each coextensive with said blade unit and respectively including said first and second surfaces, each said first and second blades including an inner surface along the length thereof, said inner surfaces combining to define said tubular passageway.

4. The laryngoscope of claim 3 wherein said inner surfaces are generally transversely concave and define a generally arcuate groove along the length of each blade.

5. The laryngoscope of claim 4 wherein each inner surface has opposed edges along the length thereof, said means for connecting said blades being defined along said edges.

6. The laryngoscope of claim 5 wherein said first tongue engaging surface is substantially rigid and transversely arcuate along the length thereof.

7. The laryngoscope of claim 6 including at least one suction passage defined longitudinally through one of said blades, said suction passage communicating with said tubular passageway at the distal end of the blade unit, and means for communicating said suction passage with a source of negative pressure.

8. The laryngoscope of claim 7 wherein said balloon includes a base pad, said balloon extending rearwardly from the distal end of said blade unit to an intermediate point along the length thereof, said pad extending rearwardly beyond said balloon to a point adjacent the proximal end of said blade unit to define a bite pad for a cushioning of the teeth of a patient.

9. The laryngoscope of claim 8 wherein said pad includes opposed longitudinally extending edges, said pad edges each including a reentrant flange along a major portion of the length thereof, including along the full length of the balloon, said second blade including opposed sides, each side having a laterally extending flange along a major portion of the length thereof rearward from the distal end, each reentrant pad edge flange engaging about one of said laterally extending flanges for a mounting of said pad and said balloon to said second blade.

10. The laryngoscope of claim 3 including at least one suction passage defined longitudinally through one of said blades, said suction passage communicating with said tubular passageway at the distal end of the blade unit, and means for communicating said suction passage with a source of negative pressure.

11. The laryngoscope of claim 10 wherein said balloon includes a base pad, said balloon extending rearwardly from the distal end of said blade unit to an intermediate point along the length thereof, said pad extending rearwardly beyond said balloon to a point adjacent the proximal end of said blade unit to define a bite pad for a cushioning of the teeth of a patient.

12. The laryngoscope of claim 11 including a handle unit defining a seat, said seat receiving the proximal end of said blade unit, means for selectively retaining the proximal end of said blade unit in said seat and precluding separation of said blades relative to each other.

13. The laryngoscope of claim 12 wherein said means for selectively inflating said balloon includes an air passage through said handle unit, means for communicating said air passage with a source of pressurized air, and means for communicating said air passage with said balloon.

14. The laryngoscope of claim 13 wherein the means for communicating said air passage with said balloon includes a blade unit airway extending from said balloon, and means in said handle unit for communicating said handle unit air passage with said blade unit airway.

15. The laryngoscope of claim 14 wherein said means for communicating said suction passage with a source of negative pressure includes a suction accommodating bore through said handle unit, means for communicating said suction bore with a source of negative pressure, and means for communicating said suction bore with said suction passage.

16. The laryngoscope of claim 15 including keying means on said blade unit and said handle unit for interengagement upon a predetermined positioning of the blade unit and handle unit relative to each other as the blade unit is received within the seat of the handle unit.

17. The laryngoscope of claim 16 including illumination means mounted on said handle unit for directing light along the length of a received blade unit.

18. The laryngoscope of claim 17 including an adapter mounted on said handle unit and selectively alignable with the proximal end of the blade unit for direct fluid communication with the tubular passageway through said blade unit, said adapter selectively receiving means for the controlled introduction of air therethrough.

19. The laryngoscope of claim 18 wherein said adapter includes window means for direct visualization through said tubular passageway upon alignment of the adapter with the proximal end of the blade unit.

20. The laryngoscope of claim 19 wherein said adapter includes a straight tube longitudinally alignable with said tubular passage, said tube having an end remote from said tubular passageway, said tube end being closed and transparent to define said window means, and a laterally directed mount on said tube inward of said window means for receiving the means for the controlled introduction of air.

21. The laryngoscope of claim 16 wherein the seat of the handle unit includes a planar base, said pad, adjacent the proximal end of the blade unit, overlying said seat base in intimate contact therewith, said seat base and said pad including pairs of complementary aligned holes comprising said means for communicating the handle unit air passage with the balloon and the means for communicating the suction bore in the handle unit with the suction passage in the blade unit.

22. The laryngoscope of claim 2 including a handle unit defining a seat, said seat receiving the proximal end of said blade unit, means for selectively retaining the proximal end of said blade unit in said seat and precluding separation of said blades relative to each other.

23. The laryngoscope of claim 22 wherein said means for selectively inflating said balloon includes an air passage through said handle unit, means for communicating said air passage with a source of pressurized air, and means for communicating said air passage with said balloon.

24. The laryngoscope of claim 23 wherein the means for communicating said air passage with said balloon includes a blade unit airway extending from said balloon, and means in said handle unit for communicating said handle unit air passage with said blade unit airway.

25. The laryngoscope of claim 24 including at least one suction passage defined longitudinally through one of said blades, said suction passage communicating with said tubular passageway at the distal end of the blade unit, and means for communicating said suction passage with a source of negative pressure.

26. The laryngoscope of claim 25 wherein said means for communicating said suction passage with a source of negative pressure includes a suction accommodating bore through said handle unit, means for communicating said suction bore with a source of negative pressure, and means for communicating said suction bore with said suction passage.

27. The laryngoscope of claim 26 wherein the seat of the handle unit includes a planar base, said pad, adjacent the proximal end of the blade unit, overlying said seat base in intimate contact therewith, said seat base and said pad including pairs of complementary aligned holes comprising said means for communicating the handle unit air passage with the balloon and the means for communicating the suction bore in the handle unit with the suction passage in the blade unit.

28. The laryngoscope of claim 2 including an adapter mounted on said handle unit and selectively alignable with the proximal end of the blade unit for direct fluid communication with the tubular passageway through said blade unit, said adapter selectively receiving means for the controlled introduction of air therethrough.

29. The laryngoscope of claim 28 wherein said adapter includes window means for direct visualization through said tubular passageway upon alignment of the adapter with the proximal end of the blade unit.

30. The laryngoscope of claim 29 wherein said adapter includes a straight tube longitudinally alignable with said tubular passage, said tube having an end remote from said tubular passageway, said tube end being closed and transparent to define said window means, and a laterally directed mount on said tube inward of said window means for receiving the means for the controlled introduction of air.

31. A method of laryngoscope manipulation for the displacement of the tongue of a patient to define an air pathway to the trachea; said method comprising the steps of providing an elongate generally rigid blade unit with a tubular passage therethrough, a length of said blade unit defining a tongue engaging surface, providing said blade unit with an inflatable section along a length thereof diametrically opposed from said tongue engaging surface, positioning said blade unit within the mouth of the patient with the inflatable section orientated toward the roof of the mouth and the tongue engaging surface in engagement with the tongue, and inflating said inflatable section into bearing engagement against the mouth roof to provide a fulcrum and effect a resultant movement of the blade unit toward the tongue with the tongue engaging surface against the tongue to effect a displacement of the tongue away from the mouth roof, establish a visual passage through the blade unit, and simultaneously establish an air pathway to the trachea while precluding the application of significant dental contact forces.

32. The method of claim 31 including the step of ventilating the patient by the pressure introduction of breathable fluid through said blade unit while retaining the blade unit in tongue displacing position and maintaining a visual passage.

33. The method of claim 32 followed by the step of introducing an endotracheal tube through said blade unit.

34. The method of claim 31 followed by the step of introducing an endotracheal tube through said blade unit.

* * * * *